US00PP21115P2

(12) United States Plant Patent
Klemm et al.

(10) Patent No.: US PP21,115 P2
(45) Date of Patent: Jun. 29, 2010

(54) ***PELARGONIUM* PLANT NAMED 'KLEPP08207'**

(50) Latin Name: *Pelargonium peltatum*
Varietal Denomination: KLEPP08207

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/383,393

(22) Filed: Mar. 24, 2009

(51) Int. Cl.
*A01H 5/00* (2006.01)

(52) U.S. Cl. ..... Plt./332

(58) Field of Classification Search ..... Plt./332
See application file for complete search history.

*Primary Examiner*—Susan B McCormick Ewoldt
(74) *Attorney, Agent, or Firm*—Jondle & Associates, P.C.

(57) ABSTRACT

A new cultivar of *Pelargonium* named 'KLEPP08207' particularly characterized by ivy *pelargonium* with brilliant red inflorescences, good, medium growth, good branching, and excellent tolerance to heat and rain, is disclosed.

1 Drawing Sheet

Genus and species: *Pelargonium peltatum.*
Variety denomination: 'KLEPP08207'.

BACKGROUND OF THE NEW PLANT

The present invention comprises a new and distinct cultivar of *Pelargonium*, botanically known as *Pelargonium peltatum*, and hereinafter referred to by the cultivar name 'KLEPP08207'. 'KLEPP08207' was discovered as a seedling resulting from a cross in July 2003 in Stuttgart, Germany between the proprietary female *Pelargonium* parent, 'KLERODER' (U.S. Plant Pat. No. 13,388) and the proprietary male *Pelargonium* parent, 'KLEP04114' (U.S. Plant patent application Ser. No. 11/349,714, now abandoned). A single plant selection was subsequently chosen for further evaluation and for asexual propagation.

The new cultivar was created in 2003 and first propagated in September 2004 in Stuttgart, Germany and has been asexually reproduced repeatedly by vegetative cuttings in Stuttgart, Germany over a four year period. 'KLEPP08207' has been found to retain its distinctive characteristics through successive asexual propagations.

Plant Breeder's Rights for this cultivar were applied for in Switzerland on Jun. 19, 2008 and in Canada on Mar. 28, 2008. 'KLEPP08207' has not been made publicly available more than one year prior to the filing date of this application.

SUMMARY OF THE INVENTION

The following are the most outstanding and distinguishing characteristics of this new cultivar when grown under normal commercial practices in a greenhouse in Stuttgart, Germany.

1. Ivy *pelargonium* with a brilliant red inflorescences;
2. Good medium growth;
3. Good branching; and
4. Excellent tolerance to heat and rain.

DESCRIPTION OF THE PHOTOGRAPH

This new *Pelargonium* plant is illustrated by the accompanying photograph which shows blooms, buds, and foliage of the plant; the colors shown are as true as can be reasonably obtained by conventional photographic procedures.

The photograph is of a plant about 3-months old taken in Spring 2008 and grown from rooted cuttings in a 12-cm pot under greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEPP08207'. The data which define these characteristics were collected from asexual reproductions carried out in Stuttgart, Germany. The plant history was taken on 3-month old plants in 12-cm pots in a greenhouse (glasshouse) in January through April 2008. The plants were pinched once at five weeks. The color readings were determined under natural light. Color references are to the R.H.S. Colour Chart of The Royal Horticultural Society of London (R.H.S.) (2001).

DETAILED BOTANICAL DESCRIPTION

Classification:
- *Family.*—Geraniacaea.
- *Species.*—*Pelargonium peltatum.*
- *Common name.*—*Pelargonium* (Geranium).
- *Denomination.*—'KLEPP08207'.

Parentage:
- *Female parent.*—The proprietary female *Pelargonium* parent, 'KLERODER' (U.S. Plant Pat. No. 13,388).
- *Male parent.*—The proprietary male *Pelargonium* parent, 'KLEP04114' (U.S. Plant patent application Ser. No. 11/349,714, now abandoned).

Plant:
- *Habit.*—Upright-later trailing.
- *Height.*—25.0 cm.
- *Spread.*—32.0 cm.
- *Life cycle.*—Spring to autumn.
- *Form.*—Round, bushy, basket.
- *Time to produce a rooted cutting.*—20 days.

*Time to bloom from propagation.*—Approximately 82 days.
*Lastingness of inflorescence on the plant.*—10 to 14 days.

Stems:
*Stem color.*—RHS 137C.
*Pubescence.*—Very weak, short hairs.
*Pubescence color.*—Greenish white.
*Stem form.*—Round.
*Diameter.*—0.5 cm to 0.6 cm.
*Length.*—8.0 cm to 12.0 cm.
*Internode length.*—About 1.0 cm to 4.0 cm.

Leaves:
*Arrangement.*—Alternate.
*Shape.*—Kidney-shaped.
*Apex.*—Round.
*Base.*—Closed.
*Margin.*—Entire.
*Surface texture* (*both sides*).—Dull.
*Length.*—4.0 cm to 8.0 cm.
*Width.*—5.0 cm to 8.0 cm.
*Color.*—Upper surface: RHS 137B. Lower surface: RHS 137C.
*Surface texture* (*both surfaces*).—Pubescent.
*Petiole.*—Length: 2.0 cm to 9.0 cm. Color: RHS 137B.
*Venation pattern.*—Palmate.
*Venation color.*—RHS 137B.

Inflorescence:
*Flowering habit.*—Continuous.
*Umbels.*—Height: 6.0 cm to 7.0 cm. Diameter: 8.0 to 9.0 cm.
*Individual florets of the umbel.*—Depth: 1.0 cm. Diameter: 4.0 cm to 5.0 cm.
*Fragrance.*—Absent.

Flower buds:
*Cluster shape.*—Round-ovate.
*Length.*—1.0 cm to 4.0 cm.
*Width.*—1.0 cm to 4.0 cm.
*Texture.*—Smooth (not pubescent).
*Bud.*—Shape: Elliptic, shell-shaped. Apex: Acute. Base: Blunt. Margin: Entire, smooth. Color: RHS 137B to RHS 137C. Size: Length: 1.0 cm to 1.8 cm. Width: 0.5 cm to 0.8 cm.

Petals:
*Quantity per flower.*—10 to 14.
*Shape.*—Drop-shaped.
*Apex.*—Round.
*Base.*—Obtuse.
*Margin.*—Entire.
*Length.*—2.5 cm.
*Width.*—1.5 cm.
*Color of lobes.*—Upper lobes (both surfaces): RHS 45A. Lower lobes (both surfaces): RHS 45B.
*Fragrance.*—Absent.

Sepals:
*Number per flower.*—5.
*Shape.*—Lanceolate.
*Apex.*—Acute.
*Base.*—Obtuse.
*Margin.*—Entire.
*Color* (*both surfaces*).—RHS 137B.
*Length.*—1.8 cm.
*Width.*—0.4 cm to 0.5 cm.

Pedicel:
*Length.*—1.8 cm.
*Diameter.*—0.15 cm.
*Color.*—RHS 137B.

Peduncle:
*Length.*—14.0 cm to 18.0 cm.
*Diameter.*—0.4 cm.
*Color.*—RHS 137C.
*Surface texture.*—Rough.

Reproductive organs:
*Stamens.*—Anther length: 0.2 cm. Filament length: 0.5 cm to 0.7 cm. Filament color: RHS 65D and RHS 66D. Pollen amount: Moderate. Pollen color: RHS 32A.
*Pistils.*—Number: 1. Stigma color: RHS 46A. Style length: Small. Style color: RHS 137D. Ovary arrangement: Central, middle.

Fruit/seed set: No.

Disease and insect resistance: Good. Typical of the species.

COMPARISON WITH PARENTAL AND COMMERCIAL CULTIVARS

'KLEPP08207' differs from the female parent, the proprietary female *Pelargonium* parent, 'KLERODER' (U.S. Plant Pat. No. 13,388) in that 'KLEPP08207' has a brilliant red flower color and a medium growth habit, while 'KLERODER' has a darker red flower color and a compact growth habit.

'KLEPP08207' differs from the male parent, the proprietary male *Pelargonium* parent, 'KLEP04114' (U.S. Plant patent application Ser. No. 11/349,714, now abandoned) in that 'KLEPP08207' has a brilliant red flower color and round leaves, while 'KLEP04114' (U.S. Plant patent application Ser. No. 11/349,714, now abandoned) has a dark red flower color and has leaves that have a more acute leaf tip.

'KLEPP08207' differs from the commercial comparison variety 'KLEP02038' (U.S. Plant Pat. No. 15,311), in that 'KLEPP08207' has a brilliant red flower color and a medium growth habit, while 'KLEP02038' has a red-purple flower color and a trailing growth habit.

I claim:

1. A new and distinct cultivar of *Pelargonium* plant named 'KLEPP08207' as shown and described herein.

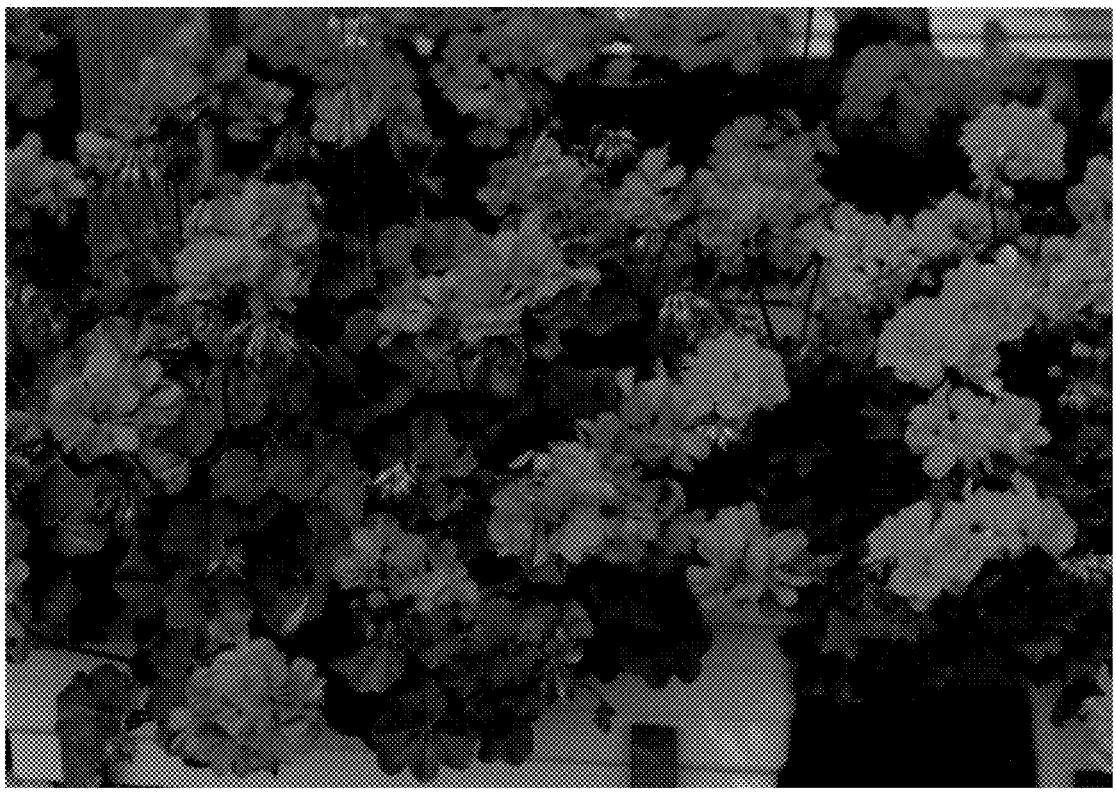

* * * * *